United States Patent [19]

Perla

[11] Patent Number: 5,496,268
[45] Date of Patent: Mar. 5, 1996

[54] INFANT MECONIUM ASPIRATING AND VENTILATING APPARATUS

[76] Inventor: Ratnavali B. Perla, 1902 Brentwood, Troy, Mich. 48098

[21] Appl. No.: 283,827

[22] Filed: Aug. 1, 1994

[51] Int. Cl.⁶ ..................................................... A61M 1/00
[52] U.S. Cl. .................. 604/27; 604/35; 604/117; 604/118; 604/902; 604/283; 128/207.14; 128/207.16
[58] Field of Search ................... 604/35, 35, 37, 604/54, 55, 73, 118, 30, 27, 117, 902, 283; 128/207.14, 207.15, 207.16

[56] References Cited

U.S. PATENT DOCUMENTS

| | | | |
|---|---|---|---|
| 2,722,932 | 11/1955 | Hickey | 604/34 |
| 4,729,765 | 3/1988 | Eckels et al. | 604/54 |
| 4,762,125 | 8/1988 | Leiman et al. | 604/35 |
| 5,269,756 | 12/1993 | Dryden | 604/54 |
| 5,279,549 | 1/1994 | Ranford | 604/34 |
| 5,354,267 | 10/1994 | Niermann et al. | 604/35 |

Primary Examiner—C. Fred Rosenbaum
Assistant Examiner—Perry E. Van Over
Attorney, Agent, or Firm—Alex Rhodes

[57] ABSTRACT

An infant meconium aspirating and ventilating apparatus comprising a flexible one-piece transparent aspirating device, a tube for connecting the aspirating device to a vacuum source, a ventilating device; and a clamp for shutting off and admitting vacuum into the suctioning device. The one-piece aspirating device, which is a primary feature of the present invention, is formed from the same piece of flexible, transparent, non-irritating plastic material, such as polyethylene. The aspirating device has an endotracheal tube end portion, an intermediate body portion, an outlet tube end portion and a port. The length of the endotracheal tube portion is preferably fixed at 13 cm. The length of the outlet tube is preferably about 35 to 50 cm. to prevent the weight and stiffness of the tube from the wall suction device from adversely affecting the maneuverability of the aspirating device. The port is used for regulating vacuum, administering medication and attaching the ventilating device.

11 Claims, 2 Drawing Sheets

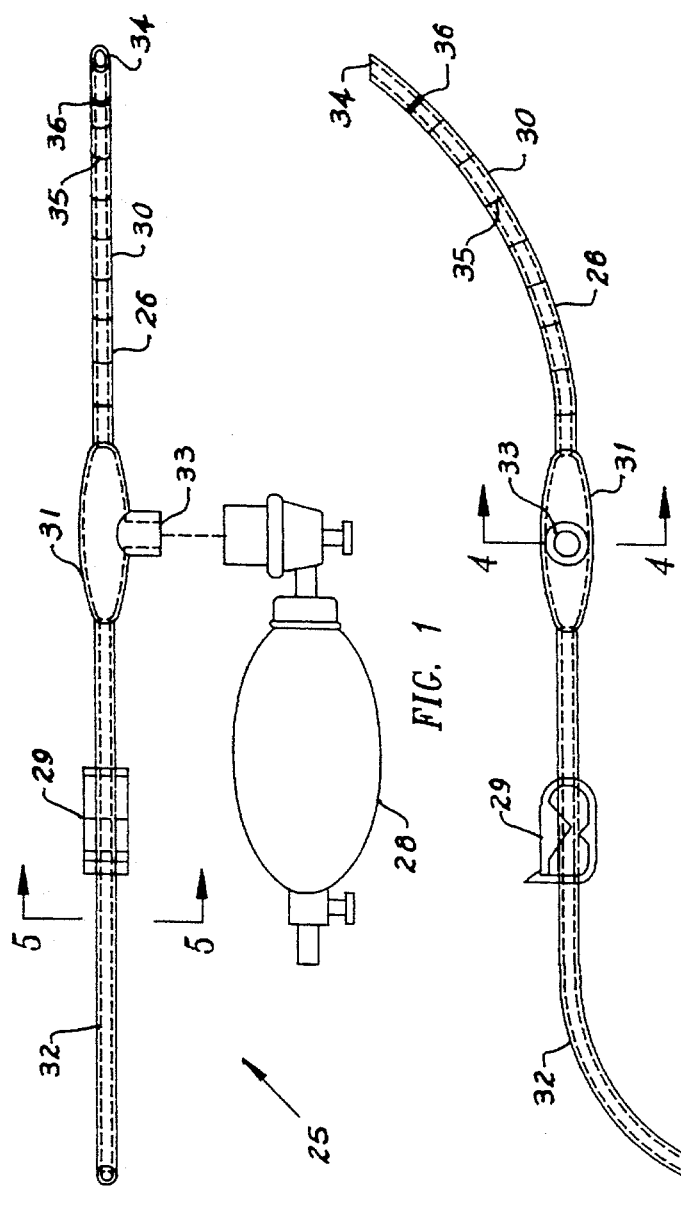
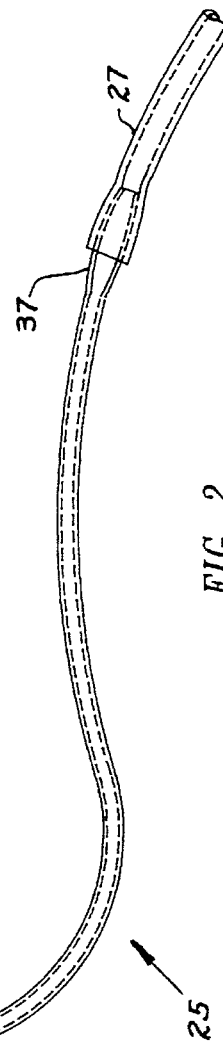
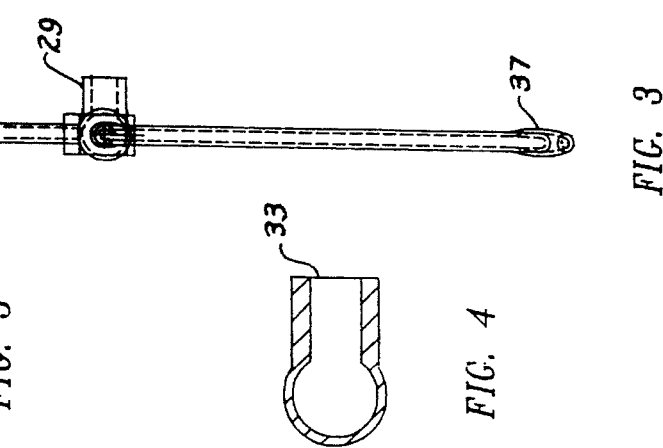
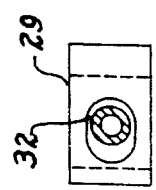

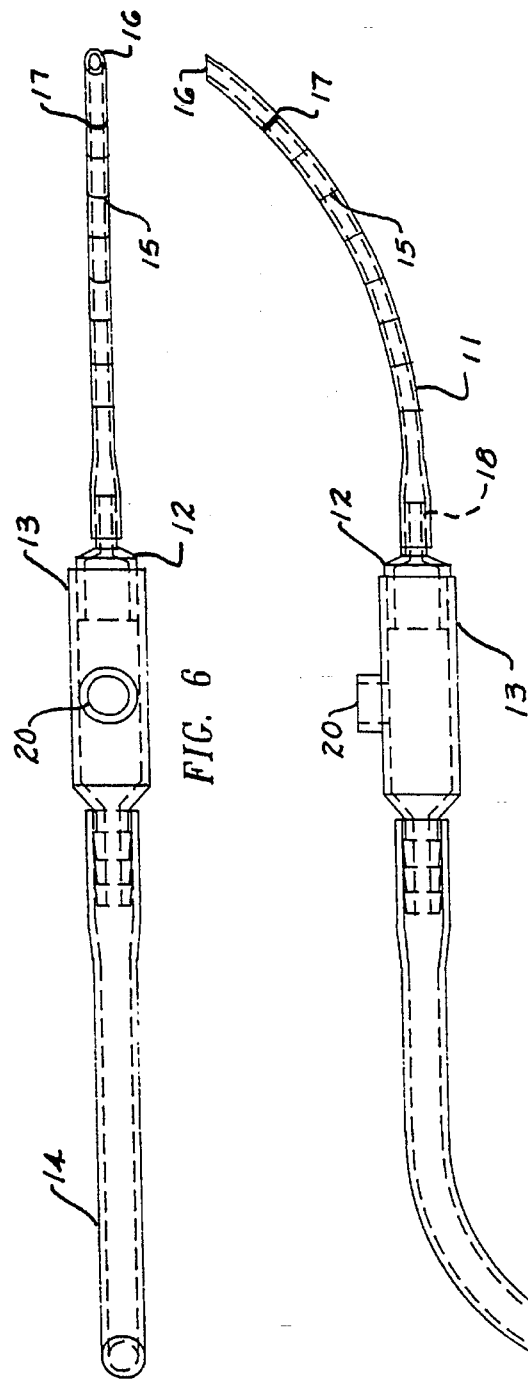
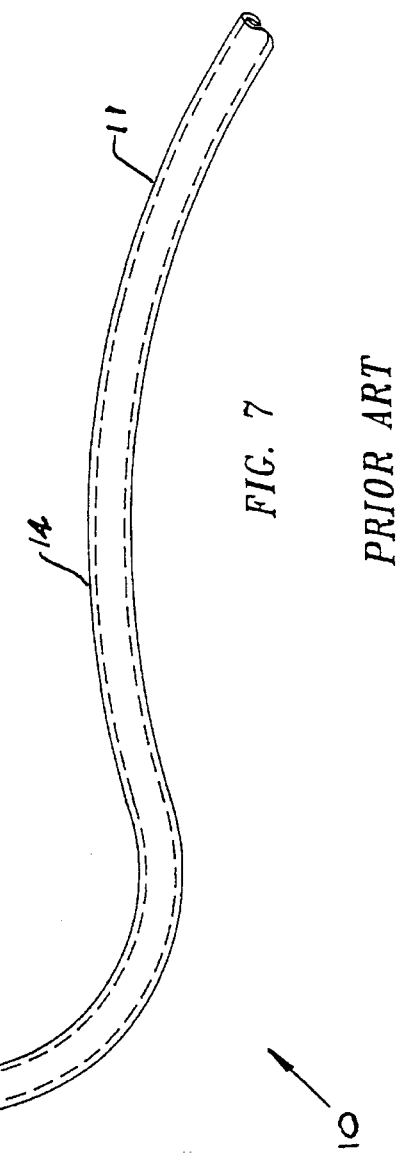
FIG. 6
FIG. 7 PRIOR ART 5,496,268

INFANT MECONIUM ASPIRATING AND VENTILATING APPARATUS

FIELD OF THE INVENTION

This invention relates to surgical aspirating and ventilating devices and more particularly to an improved apparatus for aspirating and ventilating a newborn infant immediately after a delivery.

BACKGROUND OF THE INVENTION

When meconium is present in the amniotic fluid of an infant during a delivery, there is a likelihood that this meconium will enter the airway of the newborn infant resulting in asphyxia. Asphyxia lowers blood oxygen content (hypoxemia) with a resulting fall in pH (acidosis). As long as decreased pulmonary function exists, proper oxygenation of the newborn's body tissues is impossible.

The recommended procedure during a birth is to immediately view the trachea after delivery with a laryngoscope. If thick or particulate meconium-stained fluid is present, it is extremely important to suction the fluid from the newborn as soon as possible. Asphyxia can be prevented by quickly and properly suctioning the infant and then ventilating the infant with 100% oxygen. Currently available aspirating and ventilating apparatus for newborn infants have several deficiencies.

In the recommended procedure, a conventional type endotracheal tube is shortened with a scissors and connected with a coupling to a bulky adapter. The bulky adapter is used to regulate the vacuum in the endotracheal tube and to connect the endotracheal tube via a line to a vacuum source. The vacuum source is generally a regulated wall unit.

The endotracheal tube is inserted in the trachea of a newborn infant approximately 3 cm. below the vocal chords and continuous suction is applied to remove meconium from the trachea.

After suctioning, the endotracheal tube coupling may be disconnected from the bulky adapter and a ventilating device attached to the endotracheal tube to oxygenate an asphyxiated infant.

One deficiency of the recommended practice is that the endotracheal tube is difficult to maneuver because of the bulk of the adapter and the closeness of the line from a wall vacuum source to a physician's wrist. The closeness of the line from the vacuum source imposes a load on the physician's wrist which must be overcome when maneuvering the endotracheal tube.

Another deficiency is that the endotracheal tube coupling is difficult to disconnect from the bulky adapter when it is necessary to connect a ventilating device. A third deficiency is that the apparatus has three connections between the endotracheal tube and wall vacuum source. The three connections consume time during a setting up of the apparatus and increase the likelihood of an accidental detachment of the endotracheal tube from the wall vacuum source.

A fourth deficiency is that time is required for shortening the endotracheal tube and connecting and disconnecting the endotracheal tube from the coupling and the coupling from the adapter.

A fifth deficiency is that suctioning is a two-handed operation because of the distance between the endotracheal tube and the suction regulating port.

SUMMARY OF THE INVENTION

The present invention overcomes the foregoing deficiencies by providing an aspirating and ventilating apparatus for a newborn infant which is more reliable, easier to use, and less time consuming than currently used apparatus. The invention resides in a number of features which individually and collectively contribute to its ability to remove meconium and treat asphyxia in newborn infants. These features relate to its ability to reduce the time in treating these conditions and to easily maneuver the endotracheal tube which is used for suctioning and ventilating an infant.

One benefit of the invention is that the bulky adapter is eliminated. Another benefit is that a flexible tube is provided between a physician's wrist and the line which is connected to the wall vacuum source.

The elimination of the bulky adapter and the spacing away of the endotracheal tube from the tube leading to the wall vacuum source reduces loading on the physician's wrist and increases maneuverability. A third benefit, in addition to the foregoing benefit, is that two connections between the endotracheal tube and vacuum source are eliminated. This reduces time and the likelihood of the vacuum source being detached from the endotracheal tube. A fourth benefit is that the apparatus can be operated with a single hand.

The improved aspirating and ventilating apparatus comprises a flexible one piece suctioning device in combination with a tube leading to a vacuum source; a ventilating device; and a means for shutting off vacuum when said ventilating device is operative.

The one-piece aspirating device has an endotracheal tubular portion with the large lumen of the usual type endotracheal tube, an intermediate body portion, an outlet tubular portion and a port for regulating vacuum in the endotracheal tubular portion, administering medication, and connecting said ventilating device. The aspirating device is preferably formed from the same piece of material.

Further features and benefits of the invention will become apparent from the ensuing detailed description and drawings which disclose the best mode contemplated by the inventor in practicing the invention and the property in which exclusive rights are claimed is set forth in each of the numbered claims at the conclusion of the detailed description.

BRIEF DESCRIPTION OF THE DRAWINGS

FIG. 1 is a front view of an aspirating and ventilating apparatus for a newborn infant according to the invention.

FIG. 2 is a right side elevational view of the aspirating and ventilating apparatus.

FIG. 3 is a cross-sectional view drawn to an enlarged scale taken on the line 3—3 in FIG. 2.

FIG. 4 is a cross-sectional view drawn to an enlarged scale taken on the line 4—4 in FIG. 3.

FIG. 5 is a cross-sectional view drawn to an enlarged scale taken on the line 5—5 in FIG. 1.

FIG. 6 and FIG. 7 are views of an infant's suctioning apparatus which are exemplary of the prior art.

DETAILED DESCRIPTION OF THE PREFERRED EMBODIMENT

The Prior Art

Referring now to the drawings wherein like numerals designate like and corresponding parts throughout the several views, in FIGS. 6 and 7, an infant's suctioning apparatus 10 is shown which is exemplary of the prior art. The apparatus 10 comprises a separate endotracheal tube 11, a coupling 12 for connecting one end of the endotracheal tube 11 to an adapter 13, and an adapter 13 connected at one end to the endotracheal tube 11 and at the other end to a line 14 leading to a regulated wall suction device (not shown).

The endotracheal tube 11 is marked with graduation marks 15 one cm. apart along the length of the tube 11. The purpose of the marks 15 is to assist a physician in shortening the tube 11 and to indicate whether the position of the tube 11 has changed in an infant's trachea.

The tip 16 of the endotracheal tube 11 is cut at an angle to facilitate its insertion into an infant's trachea. The tube 11 has a heavy black line 17 from 2.2 to 2.8 cm. from the end of the tip 16, called "the vocal chord guide". The heavy black line 17 is intended to be placed at the level of the infant's vocal chords.

The inside diameter of the endotracheal tube 11 ranges from about 2.5 mm. for a newborn infant to 4.0 mm. for an infant over 38 weeks in age. The length of the endotracheal tube 11 which is used varies according to the age and weight of the infant. An adhesive tape (not shown) is used to secure the endotracheal tube to the face of a newborn infant and lessens the likelihood of tube kinking.

A part of the recommended practice is to shorten the endotracheal tube 11 where it attaches to the coupling 12 with a pair of scissors so that no more than 4 cm. of the tube extends beyond an infant's lips when the tube is in the infant's trachea.

The generally cylindrical adapter 13, a bulky and rigid device, has a short inlet portion 18 which is connected to the endotracheal tube adapter 13, a short outlet portion 19 which is connected to the line 14 leading to the wall vacuum device, and an upward extending port 20 for controlling the level of vacuum in the endotracheal tube 11. The deficiencies of the current apparatus 10 can be understood by reference to FIGS. 6 and 7.

The direct connection of the line 14 from the wall vacuum device to the adapter 13 places the line 14 near a physician's wrist, resulting in the weight and relative stiffness of the line 14 loading the physician's wrist. The effect of the load on the physician's wrist is to make the small endotracheal tube to be difficult to maneuver in a newborn infant.

The three connections between the endotracheal tube 11 and wall vacuum device are also shown in FIGS. 6 and 7. The first connection 21 is between the endotracheal tube 11 and coupling 12; the second connection 22 is between the coupling 12 and bulky adapter 13; and the third connection 23 is between the bulky adapter 13 and line 14 from the wall vacuum device. A press fit of the endotracheal tube coupling 12 to the adapter 13 makes it difficult to disconnect the endotracheal tube coupling 12 from the adapter 13 when it is necessary to connect a ventilating device (not shown).

The Present Invention

With reference to FIGS. 1 through 5, inclusive, a disposable aspirating and ventilating apparatus according to the present invention is generally designated by the numeral 25. It will be observed in the drawings that the present invention 25 reduces complexity; shortens set-up time; and reduces the likelihood of a vacuum loss during the suctioning of an infant.

The improved apparatus 25 comprises a flexible one-piece transparent aspirating device 26, a tube 27 for connecting the aspirating device 26 to the vacuum source, a ventilating device, and a clamp 29 for shutting off and admitting vacuum into the suctioning device 26.

The one-piece aspirating device 26, which is a primary feature of the present invention, is best understood by reference to FIGS. 1 through 3. The aspirating device 26 is preferably formed from the same piece of flexible, transparent, non-irritating plastic material, such as polyethylene. The aspirating device 26 has an endotracheal tube end portion 30, an intermediate body portion 31, an outlet tube end portion 32 and a port 33. The design of the aspirating device 26 allows the device to be made in one piece by the low cost blow molding process.

As shown in FIGS. 1 and 2, the endotracheal tube portion 30 has an arcuate shape, an angular end portion 34, a series of graduation marks 35 and a vocal chord guide mark 36 similar to the conventional endotracheal tube 11. Only two sizes of suctioning devices 26 are contemplated for infants, one having an endotracheal tube portion 30 with a 3 mm. lumen (inside diameter) and another with a 3.5 mm. lumen. The length of the endotracheal tube portion 30 is preferably fixed at 13 cm. to eliminate the operation of shortening the tube 30.

In treating infants, it has been observed that the 13 cm. length and 3.5 mm. lumen is adequate in almost all cases. The smaller 3 mm. diam. lumen is needed in a few cases for suctioning small babies.

The outlet tube portion 32 of the aspirating device, an important feature of the invention, is preferably about 35 to 50 cm. long, to prevent the weight and stiffness of the tube 27 from the wall suction device from adversely affecting the maneuverability of the aspirating device 26.

The flexibility of the outlet tube portion 32 is greater than the tube 27 from the wall suction device because of its smaller diameter and reduced wall thickness. The outlet tube portion 32 may be formed straight or in other shapes. The free end of the outlet tube 37 is expanded and sized to attach the outlet tube portion 32 to the tube 27 from the wall suction device.

The port 33 for regulating vacuum in the endotracheal tube portion 32 extends outwardly from the side of the body portion 31, such that the port 33 is easily accessible for regulating the level of vacuum in the endotracheal tube portion 30, administering medication through the endotracheal tube portion 30 and attaching the ventilating device 28. The level of vacuum is adjusted by closing and opening the port 33 with a physician's finger.

The port 33 is sized and shaped to adequately secure the ventilating device 28 to the aspirating device 26 with a light press fit, or by some other conventional means. One benefit of the side port 33 is that the obstruction of a physician's field of vision is minimized. Another benefit is that the apparatus 25 can be operated with a single hand.

With reference to FIGS. 2 and 5, a clamp 29 is provided on the outlet tube portion 32 of the aspirating device 26 to shut off the suction when the ventilating device 28 is operative. The ventilating device 28 may be any type of conventional device for administering oxygen to a newborn infant.

The clamp 29 which surrounds the endotracheal tube portion 30 is conventional and shuts off the vacuum by pinching the outlet tube portion 32 of the aspirating device 25.

From the foregoing, it will be apparent that my invention provides an improved apparatus for aspirating and ventilating infants and in particular for suctioning thick or particulate meconium-stained fluid from newborn infants.

Although but a single embodiment has been illustrated and described, it will be appreciated that other embodiments can be provided by obvious changes in shape, materials and arrangements of parts without departing from the spirit thereof.

I claim:

1. An apparatus for suctioning and ventilating a trachea of an infant comprising: a flexible unitary aspirating and ventilating device made from a single piece of material, said aspirating device having an endotracheal tube end portion for intubating said apparatus into a trachea of an infant, an intermediate body portion communicating with said endotracheal tube portion, said endotracheal tube portion having an inside diameter of about 3.0 mm for intubating said apparatus into a trachea of an infant, and a port extending outwardly from the side of said body portion, said port communicating with said endotracheal tube portion for alternatively attaching a ventilating device or regulating the vacuum level in said endotracheal tube portion by closing and opening said port with a physician's finger in varying amounts to regulate said vacuum level in said tube portion, and a flexible outlet tube portion communicating with said body portion for operatively connecting said aspirating device to a line leading to a vacuum source; a ventilating device for supplying oxygen through said port to said endotracheal tube portion, a line for connecting said aspirating device to said vacuum source, and a means for interrupting the vacuum from said vacuum source to said endotracheal tube when said ventilating device is connected to said aspirating device.

2. The apparatus recited in claim 1 wherein said endotracheal tube portion of said aspirating device has an arcuate shape.

3. The apparatus recited in claim 1 wherein said means for interrupting said vacuum to said endotracheal tube is a clamp on said outlet tube portion of said aspirating device.

4. The apparatus recited in claim 1 wherein said outlet tube portion of said aspirating device is about 30 cm. in length.

5. The apparatus recited in claim 1 wherein said outlet tube portion of said aspirating device is between 30 and 50 cm. in length.

6. The apparatus recited in claim 1 wherein aspirating tube portion of said aspirating device has an inside diameter of about 3.5 mm. and a length of about 33 cm.

7. The apparatus recited in claim 1 wherein said aspirating device is made from a transparent material.

8. An apparatus for suctioning and ventilating a trachea of an infant consisting essentially of: a flexible unitary aspirating and ventilating device made from angle piece of material, said aspirating device having an endotracheal tube portion, said endotracheal tube portion having a small diameter for intubating said apparatus into a trachea of an infant, an intermediate body portion communicating with said endotracheal tube portion, and a port extending outwardly from the side of said body portion, said port communicating with said endotracheal tube portion for alternatively regulating the vacuum level in said endotracheal tube portion, administering medication and connecting a ventilating device, and a flexible outlet tube portion having a length of about 40 to 60 cm. for operatively connecting said aspirating device to a vacuum source; and a means for closing said outlet tube portion when a ventilating device is connected to said aspirating device.

9. The apparatus recited in claim 8 further comprising a suctioning device detachably connected to said port.

10. The apparatus recited in claim 8 further comprising a series of graduation marks and a vocal chord guide mark on an outer surface of said endotracheal tube portion to assist a physician in inserting said tube portion into an infant.

11. The apparatus recited in claim 9 wherein said endotracheal tube portion has a length of about 13 cm.

* * * * *

UNITED STATES PATENT AND TRADEMARK OFFICE
CERTIFICATE OF CORRECTION

PATENT NO. : 5,496,268
DATED : March 5, 1996
INVENTOR(S) : Ratnavali B. Perla

It is certified that error appears in the above-indentified patent and that said Letters Patent is hereby corrected as shown below:

IN THE CLAIMS:

Column 6, line 13, change "angle" to --a single--

Signed and Sealed this

Fourteenth Day of May, 1996

*Attest:*

BRUCE LEHMAN

*Attesting Officer*     *Commissioner of Patents and Trademarks*